United States Patent [19]

Sato et al.

[11] Patent Number: 4,479,937
[45] Date of Patent: Oct. 30, 1984

[54] PROCESS OF TREATING INFLAMMATION WITH HUMAN URINARY THIOL PROTEASE INHIBITOR

[75] Inventors: Hiroshi Sato, Toda; Koji Sasaki, Omiya; Kaname Takagi, Tama; Hajime Hiratani, Osaka; Yoshikazu Yuki, Kobe, all of Japan

[73] Assignee: Zeria Shinyaku Kogyo Kabushiki Kaisha, Tokyo, Japan

[21] Appl. No.: 524,549

[22] Filed: Aug. 19, 1983

[30] Foreign Application Priority Data

Feb. 24, 1983 [JP] Japan ................................. 58-29737

[51] Int. Cl.³ ............................................. A61K 35/22
[52] U.S. Cl. ..................................................... 424/99
[58] Field of Search .................................... 424/95, 99

[56] References Cited

PUBLICATIONS

Muramatsu et al., Chem. Abst., vol. 86, (1977), p. 52201m.
Sato et al., Chem. Abst., vol. 96, (1982), p. 48193z.

*Primary Examiner*—Sam Rosen
*Attorney, Agent, or Firm*—Scrivener, Clarke, Scrivener and Johnson

[57] ABSTRACT

An anti-inflammatory agent comprising as an active component an inhibitor specifically inhibiting a thiol protease, which is obtained from human urine by extraction and purification. This agent has an action of inhibiting a disease caused by a thiol protease. This anti-inflammatory agent is prepared by a process in which a thiol protease inhibitor is extracted and purified from human urine by adopting in combination at least two treatments selected from a treatment with a molecular filter, a treatment with an ion exchanger, a treatment with an adsorber and an affinity chromatographic treatment.

8 Claims, 1 Drawing Figure

U.S. Patent     Oct. 30, 1984     4,479,937
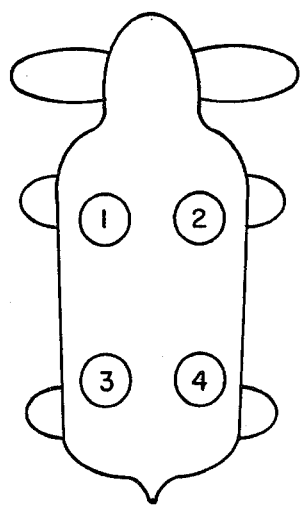

PROCESS OF TREATING INFLAMMATION WITH HUMAN URINARY THIOL PROTEASE INHIBITOR

BACKGROUND OF THE INVENTION

The present invention relates to an anti-inflammatory agent comprising as an active component a human urinary thiol protease inhibitor and a process for preparation thereof.

Human urinary proteins are composed mainly of albumin [see "Sogo Rinsho", Vol. 27, P. 1223 (1978)], and it is known that human urinary proteins contain enzymes such as urokinase or kallikrein and inhibitors such as a human urinary trypsin inhibitor as a serine enzyme inhibitor [see J. Biochem., Vol. 88, P. 1317 (1980)].

Recently, enzyme inhibitors present in human urine has been examined and a substance inhibiting ficin, a kind of a thiol protease, has newly been found [see Proc. Soc. Exp. Biol. and Med., Vol 167, P. 530 (1981)]. However, this substance has not been elucidated in detail and the biological significance of this substance has been unknown.

We, the inventors, made researches on extraction and purification of a thiol protease inhibitor from human urine and biochemical properties of this inhibitor and as the result, we found that this inhibitor is different from a urinary trypsin inhibitor and specifically inhibits the action of a thiol protease. We furthered our researches on the medicinal utility of this inhibitor and found that this inhibitor has an anti-inflammatory action. We have now completed the present invention based on these findings.

BRIEF DESCRIPTION OF THE DRAWING

The accompanying FIGURE illustrates the sites to which the anti-inflammatory agent of the present invention is administered and the modes of administering this anti-inflammatory agent.

DETAILED DESCRIPTION OF THE INVENTION

In accordance with the present invention, there are provided an anti-inflammatory agent comprising as an active component a human urinary thiol protease inhibitor which is obtained from human urine by extraction and purification, and a process for preparation of an anti-inflammatory agent comprising as an active component a human urinary thiol protease inhibitor, said process comprising extracting and purifying a thiol protease inhibitor from human urine by adopting in combination at least two treatments selected from a treatment with a molecular filter, a treatment with an ion exchanger, a treatment with an adsorber and an affinity chromatographic treatment and making the extracted and purified thiol protease inhibitor into an appropriate pharmaceutical form.

The process for extracting and purifying a thiol protease inhibitor from human urine will now be described.

Urine as the starting material may be used as it is, but it is preferred that impurities such as mucopolysaccharides in urine are precipitated and removed in advance by adjusting the pH value to 8.5 by an alkaline solution such as an aqueous solution of NaOH.

Then, urine is concentrated by ultrafiltration or the like, and fractionated by using a molecular filter such as Sephadex or Sephacryl or a molecular filtering membrane. Alternatively, urine is dialyzed with water, made adsorbed on an ion exchanger such as DEAE-cellulose or DEAE-Sephadex and eluted by a buffer solution or salt solution.

Impurities are removed from the obtained crude product of the intended substance by adopting in combination a treatment with a molecular filter such as Sephadex, Sephacryl or a molecular filtering membrane, a treatment with an ion exchanger such as DEAE-cellulose or DEAE-Sephadex, a treatment with an adsorber such as hydroxyapatite and an affinity chromatographic treatment with trypsin-Sepharose, ficin-Sepharose or papain-Sepharose, whereby a human urinary thiol protease inhibitor having an anti-inflammatory action is obtained.

The biochemical properties of the obtained huamn urinary thiol protease inhibitor will now be described.

Present substance has a molecular weight ranging from 10,000 to 100,000, and components having molecular weights of 23,000, 44,000 and 67,000 in the SDS-polyacrylamide electrophoresis mainly exhibit an anti-inflammatory action. Their isoelectric points are present at a pH value of about 4.5 to 5.0 and they are stable to treatments at acidic to alkaline pH values of from 2 to 12 and also to heat treatments at temperatures of up to 56° C., through slight degradation of the activity is observed at 65° C. Thus this substance is very stable [see "Medical Journal of Hiroshima University", Vol. 29, P. 531 (1981)].

This substance does not inhibit serine proteases such as trypsin (bovine pancreas, type III, product of Sigma Co.) and elastase (swine pancreas, type I, product of Sigma Co.) and acidic proteases such as catepsin D (product of Sigma Co.), but it specifically inhibits vegetable thiol proteases such as ficin, papain and bormelain (product of Sigma Co.) and thiol enzymes such as thiol esterase in rat blood.

The utility of this substance as a medicine will now be described.

It is known that a thiol protease specifically appears on a skin affected by hot inflammation such as Arthus inflammation or physical inflammation in allergic diseases caused by antigen-antibody reaction and that a thiol protease extracted from an inflammated skin of an affected rabbit causes similar inflammation in a non-affected rabbit and an inhibitor extracted from the inflammated skin of a rabbit inhibits inflammation. It is apparent that a thiol protease and its inhibitor have a close relation with inflammation.

Accordingly, we examined that anti-inflammatory action of an anti-inflammatory agent comprising as an effective component a human urinary thiol protease inhibitor on a skin affected by Arthus inflammation in rabbits and reverse Arthus inflammation in guinea pigs, and we confirmed that this agent is effective.

Experimental results of the inhibitory effect to Arthus inflammation in rabbits will now be described.

5 mg of bovine serum albumin (supplied by Sigma Co.) dissolved in 0.5 ml of a physiological saline solution was mixed with an equal volume of Freund's complete adjuvant and the mixture was administered to the foot pad of a rabbit (having a body weight of about 2 kg). This operation was conducted at an interval of one week. Only the rabbits in which the antibody unit by the precipitation reaction in gel was increased at least 64-fold were tested. The rabbits in which the antibody unit to bovine serum albumin was increased at least 64-fold were completely sheared on the back-site without damaging 24 hours before causing of inflammation.

Five rabbits were used for each of fractions of molecular weights of 23,000, 44,000 and 67,000 of a human urinary thiol protease inhibitor prepared in the Production Example given hereinafter. Physiological saline solutions containing 2.5 mg of bovine serum albumin alone, a mixture of 2.5 mg of bovine serum albumin and 1.5 mg or 3.0 mg of each fraction and 3 mg of each fraction alone, respectively, were hypodermically administered to the back-site near the limbs, as shown in the drawing.

After passage of 24 hours from the point of the administration, the degree of the inflammation image was examined with the naked eye. The obtained results are shown in Table 1.

TABLE 1

Inhibitory Effects of Human Urinary Thiol Protease Inhibitor to Rabbit Arthus Inflammation

| Molecular Weight | Administered Group | Degree of Unflammation Image | | | |
|---|---|---|---|---|---|
| | | only edema or flare | hyperemia added | bleeding observed | accompanied by necrosis |
| 23,000 | ① | | | 3 cases | 2 cases |
| | ② | 3 cases | 2 cases | | |
| | ③ | 4 cases | 1 case | | |
| | ④ | 5 cases | | | |
| 44,000 | ① | | | 2 cases | 3 cases |
| | ② | 1 case | 4 cases | | |
| | ③ | 3 cases | 2 cases | | |
| | ④ | 5 cases | | | |
| 67,000 | ① | | | 3 cases | 2 cases |
| | ② | 3 cases | 2 cases | | |
| | ③ | 5 cases | | | |
| | ④ | 5 cases | | | |

Note
group ① : 2.5 mg of bovine serum albumin alone administered
group ② : mixture of 2.5 mg of bovine serum albumin and 1.5 mg of each fraction administered
group ③ : mixture of 2.5 mg of bovine serum albumin and 3.0 mg of each fraction administered
group ④ : 3.0 mg of each fraction alone administered From the above results, it is seen that in the groups to which bovine serum albumin alone is administered, bleeding is apparently caused and an image of a violent vascular inflammation accompanied by necrosis is produced, while in the groups to which each fraction alone or mixture of bovine serum albumin and each fraction is administered, no bleeding is caused. Thus, it is confirmed that the anti-inflammatory agent of the present invention has a definite anti-inflammatory action.

Experimental results of the inhibitory effects to reverse Arthus inflammation in guinea pigs will now be described.

Guinea pigs (having a body weight of about 200 g) were completely sheared on the back-site 24 hours before causing of reverse Arthus inflammation, and a solution of 100 mg of bovine serum albumin dissolved in 0.5 ml of a physiological saline solution per guinea pig was intravenously injected. After lapse of 30 minutes, 5.0 mg of bovine serum albumin antibody IgG alone, a mixture of 5.0 mg of bovine serum albumin antibody IgG and 1.5 mg or 3.0 mg of each fraction of molecular weight of 23,000, 44,000 and 67,000 of a human urinary thiol protease inhibitor prepared in the Production Example given hereinafter or 3.0 mg of each fraction alone was hypodermically administered to the back-site of the guinea pigs according to the above-mentioned modes illustrated in the accompanying drawing.

After lapse of 5 hours from the point of administration, the degree of the inflammation image was examined with the naked eye. The obtained results are shown in Table 2.

As the bovine serum albumin antibody IgG, there was used a product obtained by performing the operation above-described with respect to the inhibitory effects to Arthus inflammation in rabbits, collecting and anti-serum from a rabbit in which the antibody unit was increased 128-fold and salting out the anti-serum with ammonium sulfate and purifying with DEAE-cellulose.

TABLE 2

Inhibitory Effects of Human Urinary Thiol Protease Inhibitor to Reverse Arthus Inflammation in Guinea Pigs

| Molecular Weight | Administered Group | Degree of Inflammation Image | | | |
|---|---|---|---|---|---|
| | | only edema or flare | hyperemia added | bleeding observed | accompanied by necrosis |
| 23,000 | ① | | | 5 cases | |
| | ② | 5 cases | | | |
| | ③ | 5 cases | | | |
| | ④ | 5 cases | | | |
| 44,000 | ① | | | 5 cases | |
| | ② | 4 cases | 1 case | | |
| | ③ | 5 cases | | | |
| | ④ | 5 cases | | | |
| 67,000 | ① | - | | 5 cases | |
| | ② | 5 cases | | | |
| | ③ | 5 cases | | | |
| | ④ | 5 cases | | | |

Note:
Group ① : 5.0 mg of bovine serum albumin antibody IgG alone administered
Group ② : mixture of 5.0 mg of bovine serum albumin antibody IgG and 1.5 mg of each fraction administered
Group ③ : mixture of 5.0 mg of bovine serum albumin antibody IgG and 3.0 mg of each fraction administered
Group ④ : 3.0 mg of each fraction only administered In the groups to which bovine serum albumin antibody IgG alone was administered, bleeding was observed. In contrast, in the groups to which the mixture of IgG with 1.5 mg or 3.0 mg of each fraction was administered, only edema was observed. There was no substantial difference in the anti-inflammatory action among the three fractions differing in the molecular weight.

An anti-inflammatory agent comprising as an active component a human urinary thiol protease inhibitor according to the present invention is obtained by making an injection, an ointment or the like of the human urinary protease inhibitor obtained according to the above-mentioned extraction and purification processes by adopting appropriate medicine-making means.

The amount of the human urinary thiol protease inhibitor incorporated in the anti-inflammatory agent of the present invention and the amount administered of the anti-inflammatory agent are appropriately determined according to the administration method, the administration form, the age of a patient and the disease condition. For example, in the case of an injection containing about 1 to 5 W/V % of the human urinary thiol protease inhibitor, it is ordinarily preferred that the injection be administered so that the amount administered of the inhibitor is about 10 to 100 mg/day. In other cases, the amount administered is determined according to the standard mentioned above with respect to an injection.

As is apparent from the foregoing description, the anti-inflammatory agent comprising as an active component a human urinary thiol protease inhibitor according to the present invention improves the condition of inflammation caused by a thiol protease by inhibiting this protease, and exhibits an excellent anti-inflammatory action. Accordingly, the anti-inflammatory agent of the present invention is effective for remedy of diseases in which a thiol protease participates, such as muscular dystrophy and renal hypertension. Furthermore, according to the preparation process of the present invention, the intended anti-inflammatory agent can be extracted and purified from human urine by a relatively simple operation, and mass production is possible. Moreover, since the human urinary thiol protease is obtained from human urine by extraction and purification, there arises no trouble of an antigen even if it is applied to a human body, and it is believed that the agent has a high safety with a low toxicity.

The present invention will now be described in detail with reference to the following Production Example.

Production Example:

The pH value of human urine was adjusted to a pH value of 8.5 by NaOH solution and, after formed precipitates were removed, the residual solution was sufficiently dialyzed with water. DEAE-cellulose was added to dialyzed urine in an amount of about 50 ml per 10 l of dialyzed urine, and the mixture was sufficiently stirred and packed in a column. A crude active fraction was eluted with about 100 ml of a 0.1M phosphate buffer solution (having a pH value of 7.4). The crude fraction was concentrated by ultrafiltration and subjected to the molecular filtration with a Sephacryl S-200 column, whereby the active fraction was roughly divided into two fractions having peaks of a low molecule range and a high molecule range, respectively.

The fraction of the peak of a high molecule range was made adsorbed in papain-Sephalose equilibrated with a 0.1M phosphate buffer solution (having a pH value of 7.4) and was washed sufficiently with the same buffer solution containing 0.5M of sodium chloride. The adsorbed fraction was eluted with a dilute NaOH solution (having a pH value of 12.5) and the eluted fraction was neutralized with dilute hydrochloric acid. The fraction was concentrated and subjected to the molecular filtration with a Sephadex G-150 column to divide it into two active peak fractions. By the SDS-polyacrylamide electrophoresis, it was confirmed that these fractions were composed mainly of human urinary thiol protease inhibitors having molecular weights of 44,000 and 67,000, respectively.

Separately, the fraction of the peak of a low molecule range was made adsorbed, washed and eluted in the same manner as described above. The obtained fraction was neutralized, concentrated and subjected to the molecular filtration with a Sephadex G-75 column to obtain a human urinary thiol protease inhibitor as a fraction having a peak at a position of a molecular weight of 23,000.

Franctions of molecular weights of 23,000, 44,000 and 67,000 extracted and purified according to the above-mentioned procedures were made into appropriate pharmaceutical forms alone or in combination according to customary procedures.

For the measurement of the acitivity, ficin was used as the thiol protease and casein was used as the substrate.

What is claimed is:

1. A process of treating inflammation comprising the administration of an effective amount of human urinary thiol protease inhibitor to reduce said inflammation.

2. The process of claim 1, wherein said human urinary thiol protease inhibitor has a molecular weight ranging from 10,000 to 100,000; said inhibitor is comprised of three components having the molecular weights of 23,000, 44,000 and 67,000; said components having isoelectric points that are present at a pH value of about 4.5 to 5.0; said components are stable to treatments at acidic to alkaline pH values of from 2 to 12; said components are stable to heat treatments at temperatures of up to 56° C., though slight degradation of the activity is observed at 65° C.; said inhibitor does not inhibit the serine proteases trypsin and elastase, and the acidic protease catepsin D; but said inhibitor does specifically inhibit the vegetable thiol proteases ficin, papain and bromelain, and the thiol enzyme thiol esterase in rat blood.

3. The process of claim 1, wherein said administration is by injection.

4. The process of claim 1, wherein said administration is by ointment

5. The process of claim 3, wherein said injection contains about 1 to 5 w/v% of said inhibitor and said administration is in an amount of about 10 to 100 mg./day.

6. The process of claim 1, wherein said administration is to a human subject.

7. The process of claim 6, wherein said inflammation is caused by muscular dystrophy.

8. The process of claim 6, wherein said inflammation is caused by renal hypertension.

* * * * *